United States Patent
Doi et al.

(12) 
(10) Patent No.: US 6,221,009 B1
(45) Date of Patent: Apr. 24, 2001

(54) DISPERSED-TYPE TESTING MEASURING SYSTEM AND DISPERSED-TYPE CARE SYSTEM

(75) Inventors: Shigeru Doi; Harumi Uenoyama; Yoshinori Yamaguchi, all of Kyoto (JP)

(73) Assignee: Kyoto Daiichi Kagaku Co., Ltd., Kyoto (JP)

( * ) Notice: Subject to any disclaimer, the term of this patent is extended or adjusted under 35 U.S.C. 154(b) by 0 days.

(21) Appl. No.: 09/214,966

(22) PCT Filed: Jul. 14, 1997

(86) PCT No.: PCT/JP97/02441

§ 371 Date: Mar. 9, 1999

§ 102(e) Date: Mar. 9, 1999

(87) PCT Pub. No.: WO98/02086

PCT Pub. Date: Jan. 22, 1998

(30) Foreign Application Priority Data

Jul. 16, 1996 (JP) .................................. 8-185732
Oct. 22, 1996 (JP) .................................. 8-279357
Mar. 10, 1997 (JP) .................................. 9-054780

(51) Int. Cl.$^7$ ....................................... A61B 5/00
(52) U.S. Cl. ............................... 600/300; 128/904
(58) Field of Search ........................... 600/300, 301, 600/481–486, 500, 529–532, 545–546; 128/204, 920–925

(56) References Cited

U.S. PATENT DOCUMENTS 5,410,471 * 4/1995 Alyfuku et al. ................. 600/300
5,785,650 * 7/1998 Akasaka et al. ................. 128/904
5,959,529 * 9/1999 Kail, IV ............................ 128/904

FOREIGN PATENT DOCUMENTS

| | | |
|---|---|---|
| 63-285455 | 11/1988 | (JP) . |
| 1-63861 | 3/1989 | (JP) . |
| 2-279056 | 11/1990 | (JP) . |
| 3-198832 | 8/1991 | (JP) . |
| 4-63449 | 2/1992 | (JP) . |
| 4-126441 | 4/1992 | (JP) . |
| 5-189495 | 7/1993 | (JP) . |
| 5-245117 | 9/1993 | (JP) . |
| 6-141094 | 5/1994 | (JP) . |
| 7-95963 | 4/1995 | (JP) . |
| 8-17906 | 1/1996 | (JP) . |
| 8-124037 | 5/1996 | (JP) . |

OTHER PUBLICATIONS

International Search Report for PCT/JP97/02441.

* cited by examiner

*Primary Examiner*—Cary O'Connor
*Assistant Examiner*—Michael Astorino
(74) *Attorney, Agent, or Firm*—Merchant & Gould P.C.

(57) ABSTRACT

A dispersed-type testing/measuring system provides for example a simplified terminal unit to be installed at a patient's home.

The dispersed-type testing/measuring system has a central controlling unit (20) and a plurality of terminal units 30 each accessible to the central controlling unit via a communication line (15). Each terminal unit (30) includes a crude data collecting portion (40), and a data transmitting means 45 for sending the data collected by the crude data collecting portion 40 to the central controlling unit (20). The central controlling unit 20 includes a measurement data calculating means (210) for generating measurement data by making calculation on the crude data sent from each terminal unit (30).

10 Claims, 12 Drawing Sheets

FIG.13A

Urine Analysis Is Made Now.
Please Enter Your Health Status
In One Of The Five-Grade Buttons
On The Left Hand Side. — 39

FIG.13B

Check/Examination By Your Doctor
 (Dr. xxx, xxx Dpt, xxx Hospital)
Is Recommended.
Will You Book For Your Visit Now?
Please Press Yes Or No Button. — 39

FIG.13C

Available Date/Time Options
Will Be Displayed.
Please Use Ten-keys For Selection. — 39

FIG.13D

Your Booking Is Made As Follows:
Month xxx, Date xxx, Time xxx,
Minute xxx
(Hospital xxxx, Department xxxx,
Dr. xxxx) — 39

FIG.13E

Your Doctor Will Contact You.
Please Follow His Instructions. — 39

(Terminal For Clinic: Operation/Display Portion)

DISPERSED-TYPE TESTING MEASURING SYSTEM AND DISPERSED-TYPE CARE SYSTEM

TECHNICAL FIELD

The present invention relates to a dispersed-type testing/measuring system. The dispersed-type test/measuring system can be used as a dispersed-type health care system in which a plurality of terminal units are disposed in a dispersed manner at residents of patients or small-scale clinics for sending biochemical data via communication lines to a central controlling system where the above data are maintained as personalized clinical data for each of the patients.

BACKGROUND ART

Therapy to patients suffering from diabetes, liver diseases or other chronic diseases usually takes a long period of time. At the present time, a patient of such a disease typically receive the therapy as an out patient. A problem here is that the patient has to make frequent visit to a hospital at a cost of physical burden if the disease is to be monitored closely. On the other hand, if the patient makes less frequent visit in order to relieve the physical burden of visiting, then the close monitoring of the disease becomes impossible with an increasing risk of inadequacy in treatment.

Meanwhile, a number of systems for providing health care or for helping treatment of an at-home patient have been proposed. For example, the Japanese Patent Laid-Open No. 2-279056 discloses a system in which blood sugar level data of diabetics are collected through a telephone line to a microcomputer for accumulating the data individually per patient and maintaining the data as a group data. Further, the Japanese Patent Laid-Open No. 4-63449 discloses another system in which outputs from a sensor attached to a patient's body are sent through a modem to a host computer installed at a hospital for issuing prescriptions. Further, the Japanese Patent Laid-Open No. 8-17906 discloses another system in which a toilet bowl at a home is attached with a stool testing sensor for sending excretory information to a monitoring center via a telephone line. Still Further, the Japanese Patent Laid-Open No. 3-198832 discloses another system in which diagnosis and health check are made through an audio-visual system such as the Hi-Vision system.

Each of the above prior art technologies falls into a criterion in which a medical facility or a monitoring center monitors health status of the patient while the patient is allowed to stay at home. Each of the above prior art technologies can relieve the patient of the physical burden of making visits to the medical facility. However, none of the above prior art technologies takes patients's individual differences into account when maintaining the clinical data, but instead health care instructions are made with reference only to norm values from healthy people collected as data for a group. As a result, it is difficult to provide appropriate treatment if clinical data of the patient show a change which is abnormal for this particular patient yet the change is still within a normal range obtained for the group.

Further, according to the prior art, a huge system comprising a clinical testing apparatus, a personal computer and peripherals has to be installed at a home of patient for example. This puts an economic limit to the number of patients who can afford the health care service, limiting the number of samples, which makes difficult to perform statistical maintenance of the clinical data accurately and reliably. There is another problem. Specifically, the terminal unit installed at each end such as the patient s home is calibrated initially and is capable of detecting clinical information accurately. With time however, output level of the terminal can be out of the calibration depending on environmental and operating conditions of the terminal. This reduces accuracy and reliability of the collected data, and in order to correct this problem, the terminal installed at the patient's home for example must be periodically checked and adjusted. However, if the number of terminals increases, it will become increasingly difficult to keep sending personnel for providing such periodic services.

DISCLOSURE OF THE INVENTION

It is therefore an object of the present invention to simplify the terminal unit for the dispersed-type testing/measuring system in which a plurality of testing/measuring terminal units are connected to a central controlling unit via a communication line.

Another object of the present invention is to make possible to provide more sophisticated health care to individual patients when the above dispersed-type testing/measuring system is applied as a dispersed-type health care system in which data collected at the patient's home by the terminal unit are maintained as clinical data by the central controlling unit.

Still another object of the present invention is to provide means for the central controlling unit to maintain data accurately in response to characteristic differences among the terminal units as well as changes in characteristics over time in each terminal unit.

A dispersed-type testing/measuring system provided by a first aspect of the present invention comprises a central controlling unit, and a plurality of terminal units each accessible to the central controlling unit via a communication line. Each of the terminal units includes a crude data collecting portion for collecting crude data from samples, and a data transmitting means for sending the data collected by the crude data collecting portion. The central controlling unit includes a data calculating means for generating measurement data by making calculation on the crude data sent from each terminal unit.

It should be noted here that what is meant by the term crude data collected by the crude data collecting portion of each terminal unit is an output before having significance as measurement data. Specifically, the crude data is an output from an optical, electrochemical, optical-acoustic, or other measuring means suitably selected for an object of measurement, as a conversion into electrical signals. The crude data thus collected is sent by the data transmitting means to the central controlling unit via the communication line, where analysis, adjustment, calibration and other operations are performed for finally obtaining the measurement data. Thus, the terminal unit of the dispersed-type testing/measuring system according to the present invention only includes minimum of functions for generating crude data by measuring test object samples, and for sending the crude data to the central controlling unit via the communication line, being very simple in configuration, and inexpensive in price.

According to a preferred embodiment, the crude data collecting portion further includes a maintenance-purpose crude data collecting means for collecting crude data for maintenance purpose by measuring a standard sample. Further, the central controlling unit includes a data calculating means for generating measurement data by making calculation on the crude measurement data received from each terminal unit, and a data adjusting means for adjusting the crude measurement data by comparing the maintenance-purpose crude data received from each terminal unit with a standard, or adjusting the measurement data by comparing maintenance-purpose data calculated from the maintenance-purpose crude data with a standard.

Each terminal unit collects crude measurement data by measuring a test object specimen. At the same time, predetermined standard samples are also measured for collecting the maintenance-purpose crude data. The crude measurement data and the maintenance-purpose crude data are sent to the central controlling unit via the communication line. In a system according to the present invention, a plurality of terminal units are connected to the central processing unit via the communication line. If the central controlling unit is to perform statistical processing on the measurement data, the number of the terminal unit disposed may be very huge. Even in such a case, the standard samples provided to each of the terminal unit are those of a same standard.

Now, the data collecting portion of the terminal unit can include an amplifying portion for amplifying outputs from a sensor portion. In such a case, each terminal unit may have initial setting different from the setting in others, or each terminal unit may follow a different aging process from others. These will result in different output level which will give different outputs even when the samples of the same standard are measured. Specifically, gain at the amplifying portion and amount of offset in each terminal unit may be different from those of others. According to the embodiment of the present invention, data is adjusted by comparing the maintenance-purpose data obtained from the standard sample with the standard value pre-established for the standard sample. Specifically, if the gain at the amplifying portion only is adjusted for example, ratio of the maintenance-purpose data to the standard value is taken as a coefficient of error, and this coefficient of error is used for adjusting the data obtained by the object specimen. If the adjustment is made as well to the amount of the offset, then two kinds of the standard samples are measured for identifying a function representing characteristics of the amplifying portion of the relevant terminal unit, and this function is used for adjusting the data.

With the above arrangement, even if the number of the testing/measuring terminal units becomes very huge and errors in measurement data becomes significant due to characteristic differences among the terminal units as well as changes in characteristics over time in each of the terminal units, there is no need for performing maintenance service to each of the terminal units. Instead, the central processing unit can centrally correct errors included in the data for accumulating accurate measurement data.

According to the preferred embodiment, the crude data collecting portion of each terminal unit further includes a calibration-purpose crude data collecting means for collecting calibration-purpose crude data necessary for calculating the measurement data from the crude measurement data. Further, the central controlling unit includes a data calculating means for generating the measurement data from the crude measurement data received from each terminal or the crude measurement data adjusted by the data adjusting means and the calibration-purpose crude data received from each terminal unit.

Specifically, if the system is arranged for measuring concentration of a specific chemical component contained in urine by means of spectrum analysis for example, each terminal unit is pre-loaded not only with the above standard sample which is used primarily for centrally correcting errors resulting from differences in output level of the amplifying portion, but also with preferably a plurality of calibration-purpose samples each having a predetermined rate of concentration. By using calibration-purpose crude data obtained from these samples, the central processing unit makes a calibration curve, according to which calculation is made for obtaining concentration of the specific component in the measurement specimen, i.e. the urine sample loaded by the patient. Again in this case, all the crude data are adjusted for error as already described. Thus, despite the differences in characteristics present in the amplifying portions, the accumulated measurement data is very accurate. Here again, the term crude data means an output before having significance as clinical data as used in clinical testing. The crude data thus collected is sent to the central controlling unit via the communication line, where the above described adjustment on the data is made, and then analysis/calculation (calibration) are performed for finally obtaining the measurement data having significance as clinical data.

According to the preferred embodiment, the crude data collecting portion of each terminal unit includes an output level adjusting portion activated by a command from the central controlling unit, and the central controlling unit includes a terminal-unit data output level adjusting means for issuing the command for making a predetermined adjustment to the data output level if the maintenance-purpose crude data received from each terminal unit has a deviation from the standard not smaller than a predetermined value. The adjustment to the data output level is made so that there is no deviation from the standard value for the maintenance-purpose crude data. Even if the above adjustment on the output level cannot totally eliminate the error in the maintenance-purpose crude data, accuracy of the measurement data can be assured by using the above described data adjustment means provided in the central controlling unit as well.

According to the preferred embodiment, the central controlling unit includes an alarming means for notifying of abnormality of the terminal units if the maintenance-purpose crude data received from respective terminal units or the maintenance-purpose data calculated for respective terminal units has a deviation from the applicable standard not smaller than a predetermined value.

In the above case, the terminal unit has become out of calibration to an extent where the measurement data cannot be corrected by the adjustment to the terminal data output level or by the data adjusting operation performed in the central controlling unit. Such alarm is issued to a system maintenance company and terminal unit for example. This is an occasion when the relevant terminal unit is first visited by service personnel for inspection and maintenance.

According to a second aspect of the present invention, a dispersed-type health care system using the dispersed-type testing/measuring system according to the above first aspect is provided. According to this dispersed-type health care system, each terminal unit is assigned to a patient or a medical facility. Each terminal unit includes a clinical test crude data collecting portion, and a data transmitting means for sending the crude data collected by the clinical test crude data collecting portion to the central controlling unit. Further, The central controlling unit includes a clinical data calculating means for generating clinical data by making calculation on the clinical test crude data sent from each terminal unit and/or a personalized clinical data maintaining means for monitoring health status of the patient assigned with each terminal unit.

According to the preferred embodiment, each terminal unit includes the clinical test crude data collecting portion or further includes a health status information entering portion. The data transmitting means transmits only the clinical test crude data collected by the clinical test crude data collecting portion or health status data entered from the health status information entering portion as well. The central controlling unit includes a clinical data calculating means for generating clinical data by making calculation on the clinical test crude data sent from each terminal unit and a personalized clinical data maintaining means for monitoring health status of the patient assigned with each terminal unit.

The central controlling unit obtains clinical data by analyzing/calibrating the crude data sent from each terminal unit. The personalized clinical data maintaining means provided in the central controlling unit uses the clinical data for centrally monitoring health status of the patients through corresponding terminal units.

As described earlier, the terminal unit used in the dispersed-type testing/measuring system according to the present invention can have a remarkably simpler configuration than the terminal units in many prior art systems proposed as an at-home treatment supporting system. Therefore, the terminal unit according to the present invention can be inexpensive enough, so that many of those patients hoping to have the at-home treatment supporting service or at-home health care service can afford such a service without bearing a heavy economic burden.

Further, it becomes possible that a plurality of patients receive such a service at a clinic for example. This makes possible to increase the number of samples included in statistical processing of the clinical data, leading to more accurate clinical statistics which can make a big contribution to advancement of medical treatment.

As described earlier, according to the preferred embodiment, each of the above terminal unit is provided with the health status information entry portion. Each terminal unit automatically generate clinical test crude data when samples are loaded, and send this crude data to the central controlling unit for calculation of the clinical data and for personalized clinical data maintenance as already described. In addition to this, if an arrangement is made so that the patient can enter his own assessment on his current health status in five grades for example, then it becomes possible for the personalized clinical data maintenance means of the central controlling unit to monitor the health status of the patient more closely.

According to the preferred embodiment, the central controlling unit further includes a group statistic processing means for determining a range of normality for a group by processing clinical data with respect to a plurality of terminals.

As described earlier, the terminal unit according to the present invention can be made relatively inexpensively. Thus, it becomes possible to centrally monitor a large number of terminal units and the patients assigned to the terminal units. In such a case, by accumulating the clinical data obtained from all of the terminal units as a population, it becomes possible to perform statistical processing of the clinical data at a higher accuracy.

The personalized clinical data maintaining means can be provided with a personalized statistical processing means for determining a personalized range of normality by statistically processing the clinical data with respect to a specific terminal unit.

Specifically, there can be a case in which clinical data of a specific patient is changing within a normal range established upon a large population, yet the change is abrupt for that particular patient. In such a case that abrupt change should be interpreted as an indication of abnormality developing in the patient. By providing the personalized statistical processing means as above, it becomes possible to provide even closer health care such as identifying abnormality at a personalized level as described above. Further, as described earlier, an arrangement can be made for having personal input by the patient on his health status entered from the health status information entry portion of the terminal unit. By making reference to such health status information, it becomes possible to provide even more closer and accurate monitoring in finding abnormality at a personal level.

The personalized clinical data maintaining means may include an abnormality judging means for judging if the clinical data calculated from the crude data sent from each terminal unit is abnormal or not with respect to the range of normality for the group and/or the range of normality for respective patients. Further, the personalized clinical data maintaining means may further include an alarming means for issuing an abnormality report to a relevant terminal unit and/or to a medical facility accessible by the central controlling unit via the communication line if the abnormality judging means judges for abnormality to be present.

The personalized clinical data maintaining means can further include an abnormal clinical data forwarding means for forwarding abnormal clinical data to the medical facility accessible by the central controlling unit via the communication line if the abnormality judging means judges for abnormality to be present.

In judging if the clinical data calculated from the clinical data sent from each terminal unit is abnormal or not with respect to the range of normality for the group and/or the range of normality for respective patients, it is of course possible to make such an arrangement as the abnormality judging means takes into account the accompanying health status data sent from respective terminal units.

With the above arrangement, sophisticated health care to an at-home patient becomes possible. Specifically, upon receiving the above abnormality report through the terminal unit, the patient can make contact with a medical facility for appropriate treatment. On the other hand, an attending physician, upon receiving the same abnormality report at the medical facility, can take prompt actions such as contacting the patients or family members for giving appropriate instructions. In such a case where the medical facility is also forwarded with the above abnormal clinical data, the attending physician can make more appropriate instructions.

A dispersed-type health care system provided by a third aspect of the present invention comprises a central controlling unit and a plurality of terminal units each accessible to the central controlling unit via a communication line. Each terminal unit is assigned to a patient or a facility. Each of the terminal units includes a clinical test crude data collecting portion, a hospital visit booking display/entry portion, and a data transmitting means for sending the clinical test crude data collected by the clinical test crude data collecting portion. The central controlling unit includes a clinical data calculating means for calculating clinical data from the clinical test crude data sent from each terminal unit, and a personalized clinical data maintaining means for maintaining health information of the patient with respect to each terminal unit. The central controlling unit further includes a hospital visit booking handling means for the central controlling unit to check booking status of a medical facility accessible via the communication line for sending data on available dates and times to each terminal unit, and to receive booking entry data entered from the hospital visit booking display/entry portion of each terminal unit for forwarding the booking entry data to the medical facility.

Specifically, the dispersed-type health care system according to this third aspect makes possible to book a visit to medical facility through the terminal unit installed at the patient's home. For example, in the dispersed-type health care system according to the second aspect of the present invention, if the at-home patient receives an abnormality report through the terminal unit from the central controlling unit, or advised by the attending physician to make a visit, then the patient or his family members for example can book for the visit right at home, through the terminal unit. This makes possible to take a quicker and more appropriate clinical action if abnormality is found in the at-home patient.

According to the preferred embodiment, if the clinical data indicates abnormality in the at-home patient, the central controlling unit automatically makes inquiry into the booking status of the medical facility, sends data on available time and date options to the terminal unit, and makes abnormality report while prompting the patient to visit the medical facility. The patient or his family member for example can then readily choose from the available time and date options and make an entry, completing the booking procedure right at the moment.

Other features and advantages of the present invention will become clearer from the detailed description to be made below with reference to the accompanying drawings.

BRIEF DESCRIPTION OF THE DRAWINGS

FIG. 13 shows some sample displays to be made on the operation/display portion of the terminal unit to be installed at home.

BEST MODE FOR CARRYING OUT THE INVENTION

Figure 1:
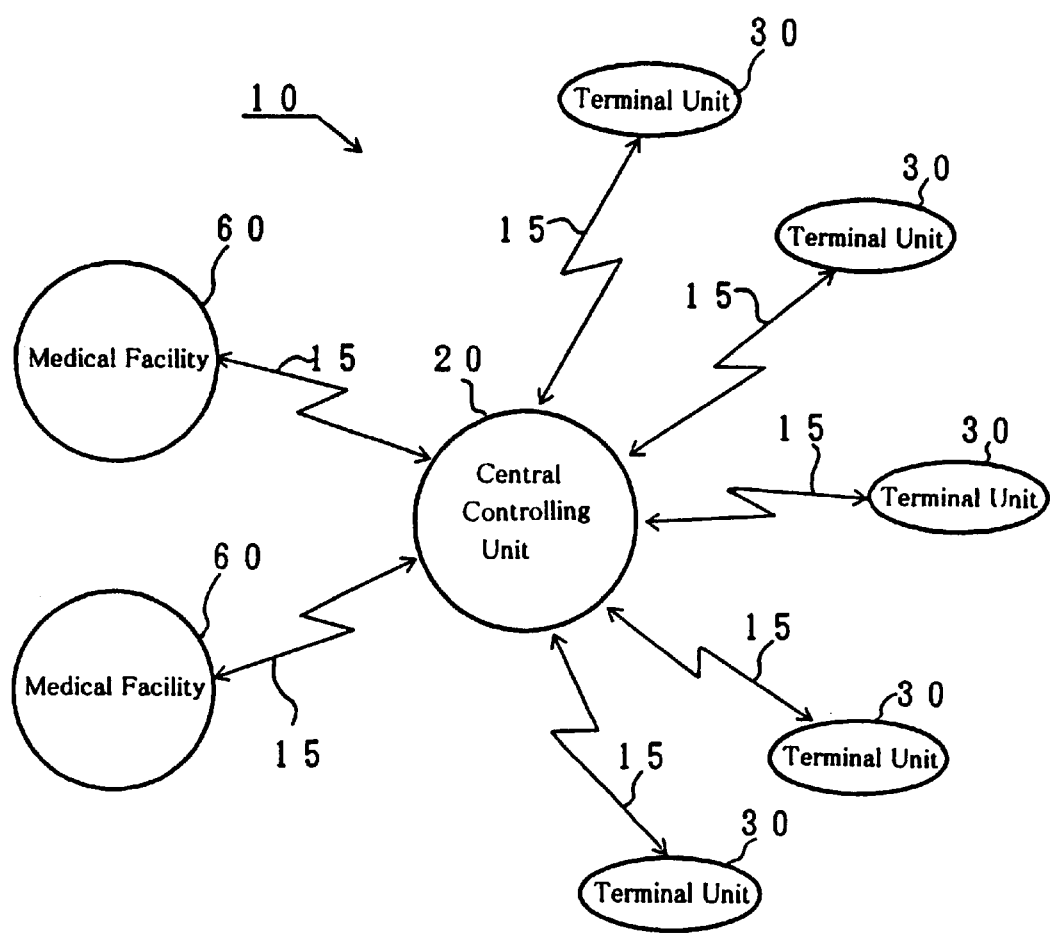
FIG. 1 is a conceptual diagram of a dispersed-type health care system according to the present invention.

FIG. 1 shows a concept of an embodiment of the dispersed-type testing/measuring system according to the present invention. This concept is for a dispersed-type health care system 10.

This dispersed-type health care system 10 comprises a central controlling unit 20, and a plurality of terminal units 30 each accessible to the central controlling unit 20 through a communication line 15. The central controlling unit 20 may be installed in a high level medical caring facility such as a university hospital, or in a separate facility such as a monitoring center which is independent from a medical caring organization. Each of the terminal units 30 is installed principally at a home of a patient. However, the installation may also be made at a small-scale medical caring facility such as a clinic in a depopulated area.

If the central controlling unit 20 is to be independent from a high level medical caring facility, as shown in FIG. 1, the central controlling unit 20 is made accessible through the communication line 15 to a high level medical caring facility 100 such as a university hospital or other medical caring facilities staffed by attending physician of respective patients so that information from the dispersed-type health care system 10 can be quickly reflected to treatment of each patient for example. The communication line 15 is generally a network of public phone lines, but may alternatively be a special network such as Internet depending on a situation.

Figure 2:
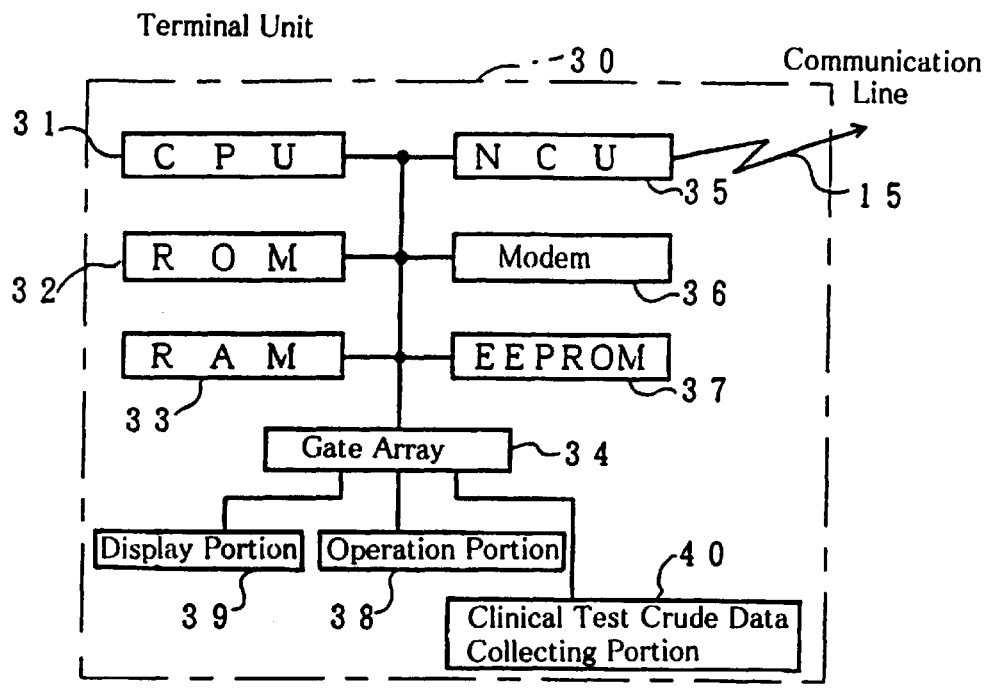
FIG. 2 is a block diagram of a terminal unit.

FIG. 2 is a block diagram showing a configuration of the terminal unit 30.

This terminal unit 30 comprises minimum necessary sizes of a CPU 31, a ROM 32, a RAM 33, a gate array 34, an NCU 35, a modem 36, an EEPROM 37, an operation portion 38, a clinical test crude data collecting portion 40, and a display portion 39 respectively. The CPU 31, ROM 32, RAM 33, gate array 34, NCU 35, modem 36 and EEPROM 37 are mutually connected by a bus line. The gate array 34 is connected by the operation portion 38, display portion 39 and clinical test crude data collecting portion 40. The NCU 35 is connected to the modem 36 and the communication line 15. It should be noted that the clinical test crude data collecting portion 40 includes a maintenance-purpose crude data collecting means 50 and a calibrating-purpose crude data collecting means 51, each to be described later.

The CPU 31 provides over all control to the terminal unit 30. The ROM 32 stores various programs. The RAM 33 memorizes variety of data processed by the CPU 31. The gate array 34 controls input and output to and from the CPU 31. The NCU 35 is connected to the communication line and provides network control. The modem 36 demodulates incoming data, while modulating outgoing data. The EEPROM 37 memorizes flags and other information. The operation portion 38 includes key switches for example. The display portion 39 includes an LCD for example for displaying various information controlled by the CPU 31.

Figure 3:
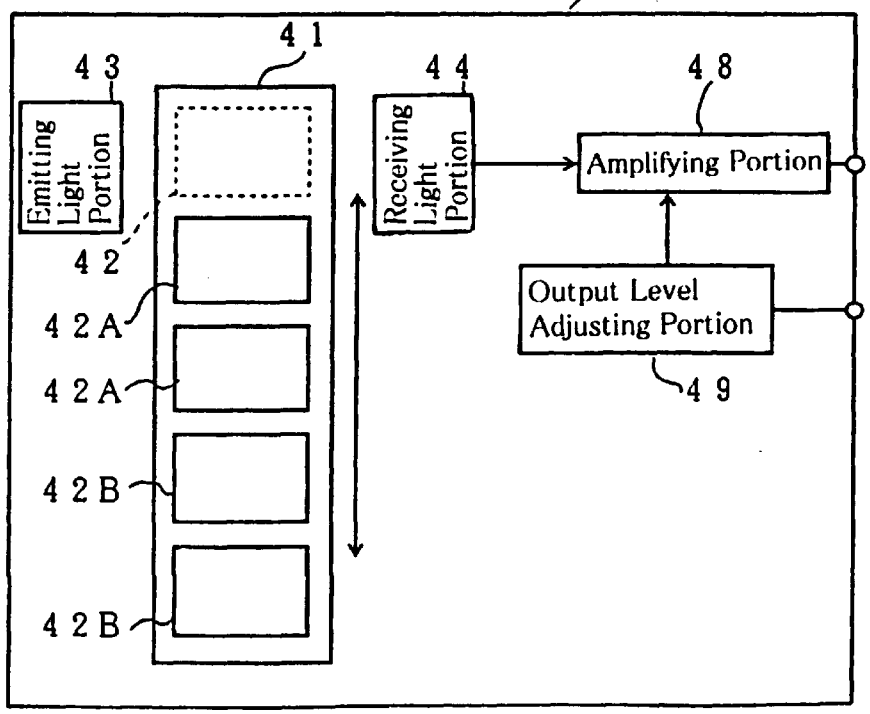
FIG. 3 is a schematic diagram showing a configuration of a crude data collecting portion included in the above terminal unit.

The clinical test crude data collecting portion 40 collects crude data by analyzing urine of a patient for a specific chemical component through spectrum analysis for example. It should be noted however, that according to the present invention, the clinical test crude data collecting portion 40 does not perform calculation for quantifying the chemical component. Instead, the quantifying calculation for converting the crude data into clinically meaningful data is performed by a clinical data calculating means 210 included in the central controlling unit 20 as to be described later. Specifically, according to the present invention, the clinical test crude data collecting portion 40 provided in the terminal unit 30 and the clinical data calculating means 210 provided in the central controlling unit 20 work together providing a virtual clinical testing apparatus. (See FIG. 7.) FIG. 3 is a schematic diagram showing a configuration of the clinical test crude data collecting portion 40 included in the terminal unit 30. This clinical test crude data collecting portion 40 collects crude data for determining concentration of the specific chemical component contained in the urine of the patient through spectrum analysis. A slidable sample magazine 41 can load a plurality of samples. A first sample loaded in the sample magazine 41 is the urine of the patient (measurement speciment) 42. The urine is loaded as packed in a predetermined cell. A second sample is a standard sample 42A for obtaining maintenance-purpose crude data for adjusting errors included in outputs from an amplifying portion 48 due to shift in output level. This standard sample 42A may be made of a plate of glass for example, and further may be made of a plurality of samples. A third sample is a calibration-purpose sample 42B for obtaining calibration-purpose crude data for making calculation (calibration) on the crude data collected by the terminal unit 30 for obtaining clinically meaningful data. This calibration-purpose sample 42B is a dummy or true sample containing the specific chemical component at a predetermined rate. More preferably, a plurality of calibration-purpose samples are prepared, each containing the specific chemical component at a different rate from that of the other, for the central controlling unit 20 to make a calibration curve. Depending on situations, part of the standard sample may be used as the calibration-purpose sample. The above standard sample 42A and the calibration-purpose sample 42B are prepared for each of the terminal unit 30 as a standardized samples.

The sample magazine 41 slides between a light emitting portion 43 and a light receiving portion 44, transporting each of the above samples to a measuring position. When a measurement is made, signals representing the intensity of light received by the light receiving portion 44 is outputted via the amplifying portion 48. More specifically, the clinical test crude data collecting portion 40 outputs via the amplifying portion 48 signals representing the intensity of light of a selected wave length before entering and after passing each of the samples. It should be noted here that the specific wave length of light can be selected by providing a plurality of color filters at the light emitting portion. Alternatively, a spectroscope may be provided for allowing a predetermined spectrum of light beamed to the samples. Further, LED's emitting different colors of beam such as red, blue and green may be used, or a laser diode may be used as a light source.

Thus, electric signal output made for the urine sample is the measuring-purpose crude data. Likewise, electric signal output made for the standard sample is the maintenance-purpose crude data, and electric signal output made for the calibration sample is the calibration-purpose crude data. Further, as shown in FIG. 3, according to this embodiment, an output level of the amplifying portion 48 can be adjusted by an output level adjusting portion 49. The output level adjusting portion 49 is activated by a command from the central controlling unit 20 as will be described later. Each of the crude data obtained as described above is sent to the central controlling unit 20 via the modem 36 and communication line 15.

Figure 4:
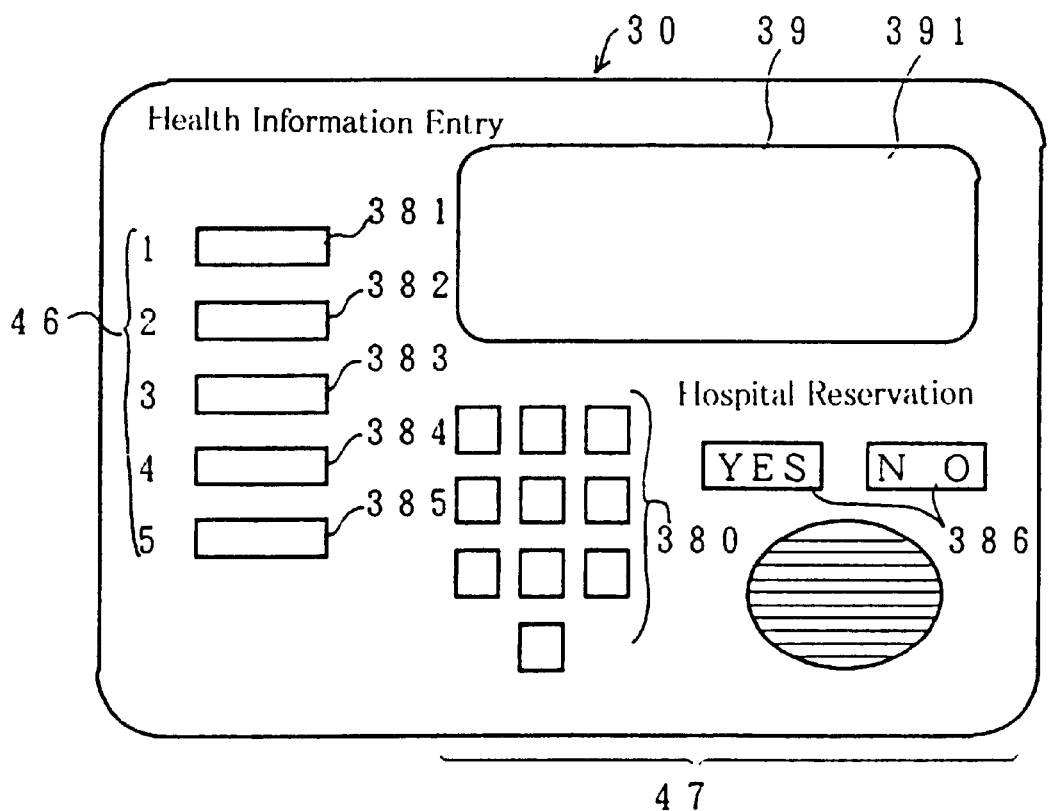
FIG. 4 is a front view of an operation/display portion of a terminal unit to be installed at home.

FIG. 4 shows an operation/display portion of the terminal unit 30 to be installed at the patient's home. Numeric codes 381 through 385 represents a set of five key switches for entering health information through which the patient can grade and enter his current health status at each occasion. A numeric code 380 represents a set of key switches for entering various additional information. A numeric code 386 represents a set of information entry switches for making reservation for a visit to a hospital for example. A numeric code 391 represents an LCD panel for displaying various information. Specific actions and steps for using this operation/display portion will be described later.

Figure 5:
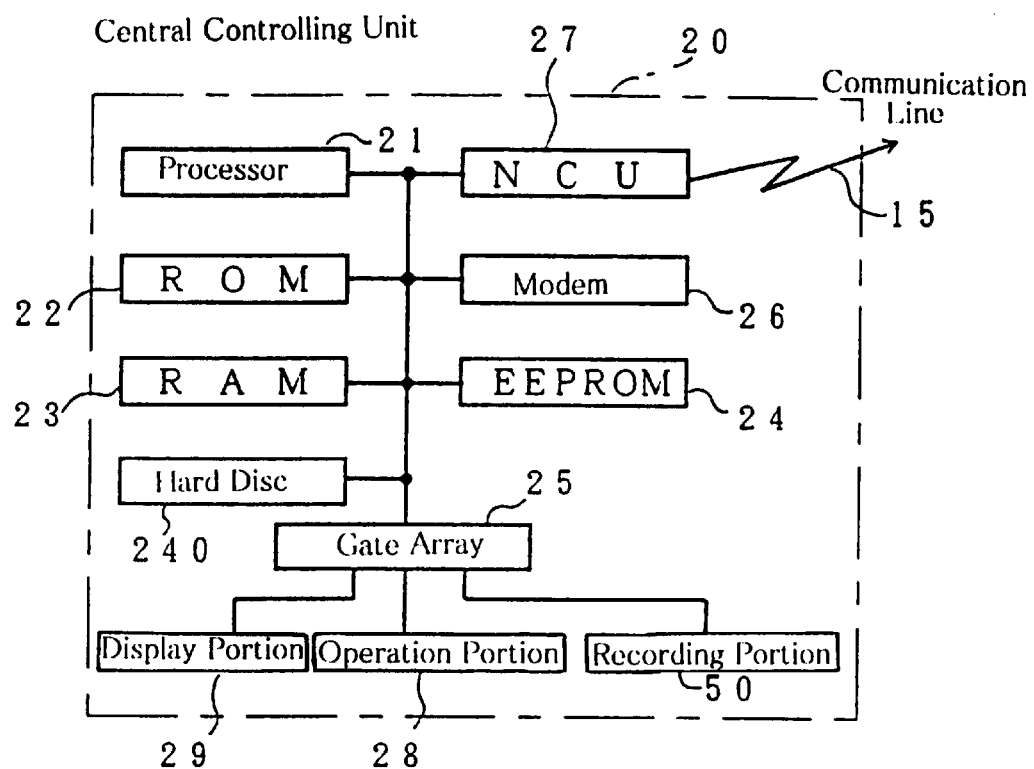
FIG. 5 is a block diagram of a central controlling unit.

FIG. 5 is a block diagram showing a configuration of the central controlling unit 20. This central controlling unit 20 is basically a mainframe computer capable of performing communications and data processing, comprising specifically a processor 21, memories such as a ROM 22, a RAM 23, an EEPROM 24 and a hard disc 240, a gate array 25, a modem 26, an NCU 27, an operation portion 28, a display portion 29, and recording portion 50, and so on. The processor 21, ROM 22, RAM 23, hard disc 240, gate array 25, EEPROM 24, modem 26 and NCU 27 are mutually connected by a bus line. The gate array 25 is connected by the operation portion 28, display portion 29 and recording portion 50. The NCU 27 is connected to the modem 26 and communication line 15.

Figure 6:
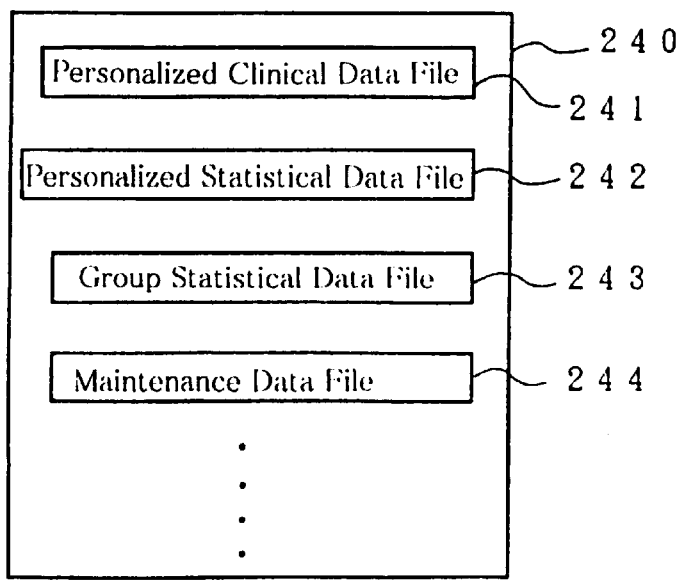
FIG. 6 is a schematic diagram showing a use of a hard disc memory included in the central controlling unit.

The processor 21 provides over all control to the central controlling unit 20. The ROM 22 stores various programs and data. The RAM 23 memorizes variety of data processed by the processor 21. The gate array 25 controls input and output to and from the processor 21. The EEPROM 24 memorizes flags and other information. The modem 26 demodulates incoming data, while modulating outgoing data. The NCU 27 is connected to the communication line and provides network control. The operation portion 28 includes groups of entry switches for outputting command signals according to operation made by an operator. The display portion 29 includes a CRT for example for displaying various information controlled by the processor 21. The recording portion 50 records various data on paper. As shown in FIG. 6, the hard disc 240 is a large capacity memory including personalized clinical data file 241 for storing personalized clinical data, personalized statistical data file 242, group statistic data file 243, maintenance data file 244 for maintaining each terminal, and so on.

Figure 7:
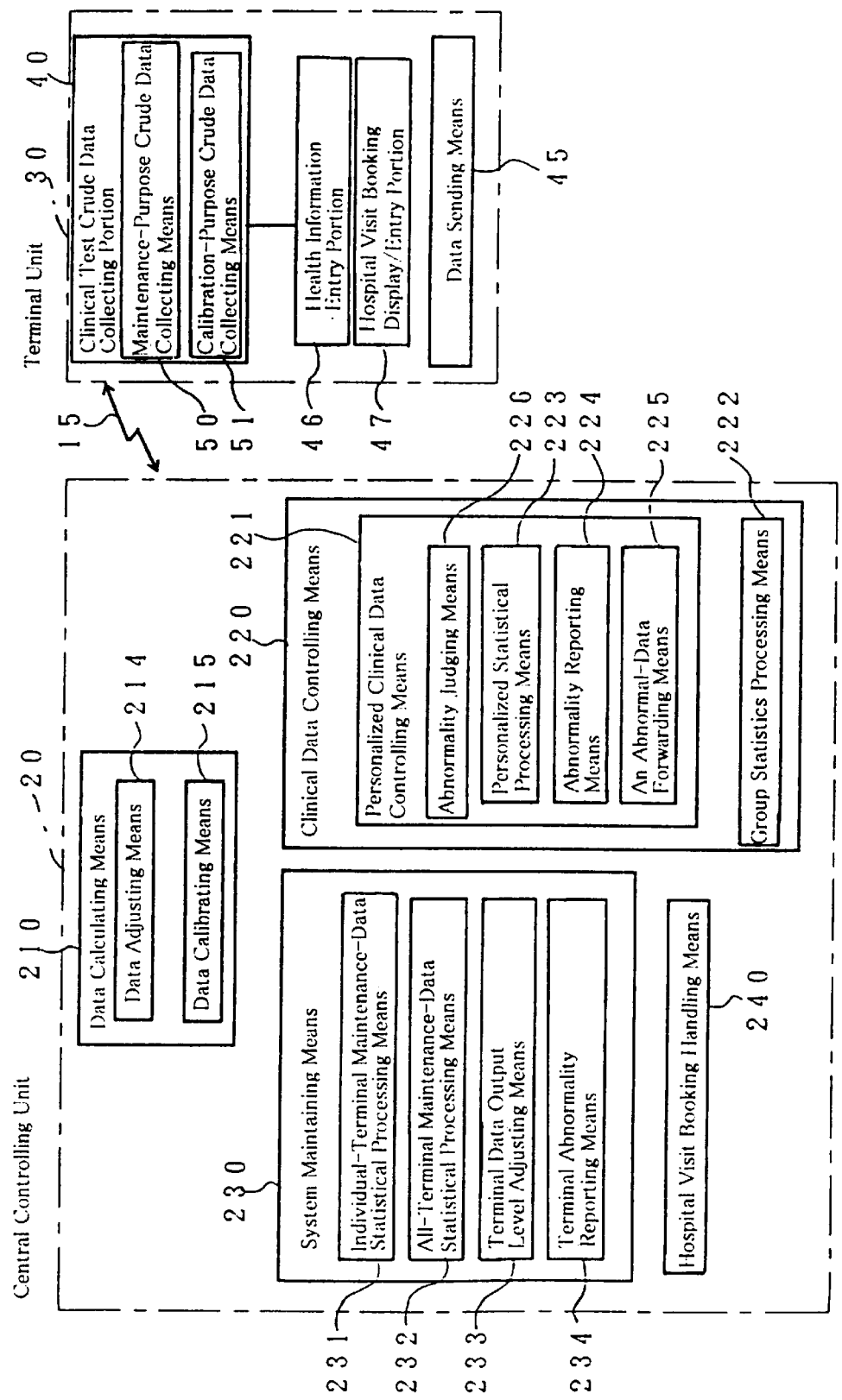
FIG. 7 is a block diagram showing functions of the terminal unit and the central controlling unit as part of the dispersed-type health care system.

As shown in a block diagram in FIG. 7, the central controlling unit 20 is given a various functions virtually realized by programs. Specifically, these functions may be roughly divided into; the clinical data calculating means 210 for calculating clinical data from various crude data sent from each of the terminal units 30; a clinical data controlling means 220 for performing personalized statistical management for each patient by using the obtained clinical data; a booking handling means 240 for allowing the central controlling unit 20 to check booking status of the medical facilities 100 accessible through the communication line, send booking availability data to respective terminal units 30, receive booking entry data entered from the reservation display/entry portion 386 of respective terminal units 30, and forward the reservation entry to the above medical facility; and a system maintaining means 230 for maintaining the maintenance data and performing statistical operations for each of the terminal units 30.

According to the present embodiment, the clinical data calculating means 210 includes a data adjusting means 214 for making adjustment by using the maintenance-purpose crude data on errors included in the data from the terminal unit 30 due to the shift in the output level of the terminal unit, and a data calibrating means 215 for calculating (calibrating) the measured data (clinical data) from the crude measurement data and the calibration-purpose crude data sent from each terminal unit 30.

According to the present embodiment, the clinical data controlling means 220 includes a personalized clinical data controlling means 221 for monitoring health status of the patients respectively assigned with the terminal units 30, and a group statistics processing means 222 for statistically maintaining the clinical data, performing such operations as determining a range of normality for a group of patients. The above personalized clinical data controlling means 221 includes; a personalized statistical processing means 223 for statistically processing personal clinical data, performing such operations as determining a range of normality for each of the individual patients respectively assigned with the terminal units 30; an abnormality judging means 226 for judging if the clinical data calculated from the crude data sent from respective terminal units 30 is abnormal or not with respect to the normal range for the group and/or the range for a particular patient; an abnormality reporting means 224 for issuing an abnormality report if the data was found abnormal; and an abnormal-data forwarding means 225 for allowing the central controlling unit 20 to forward the abnormal data to the medical facilities 60 accessible via the communication line 15 if the clinical data calculated from the crude data sent from respective terminal units 30 is abnormal with respect to the normal range for the group and/or respective normal ranges for individual patients.

According to the present embodiment, the system maintaining means 230 includes; an individual-terminal maintenance-data statistical processing means 232 for statistically processing the maintenance data individually for each of the terminals; an all-terminal maintenance-data statistical processing means 231 for statistically processing the maintenance data of all the terminals; a terminal data output level adjusting means 233 for issuing an output level adjusting command if the maintenance-purpose crude data sent from respective terminal units 30 fall in a predetermined range of conditions; and a terminal abnormality reporting means 234 for warning of terminal unit abnormality if the maintenance-purpose crude data sent from respective terminal unit 30 indicates a problematic or abnormal status of the terminal unit. The terminal unit 30 includes; the clinical test crude data collecting portion 40; a health information entry portion 46 through which patient's health status can be entered by means of a five-graded scale for example; a hospital visit booking display/entry portion 47 through which a booking request for a visit to the medical facility 100 can be entered; and a data sending means 45 for sending the clinical testing crude data collected by the clinical test crude data collecting portion 40 and if applicable the health status data entered through the health information entry portion 46 to the central controlling unit 20. Further, the clinical test crude data collecting portion 40 is provided with the maintenance-purpose crude data collecting means 50 and the calibrating-purpose crude data collecting means 51 as has been described above.

Figure 8:
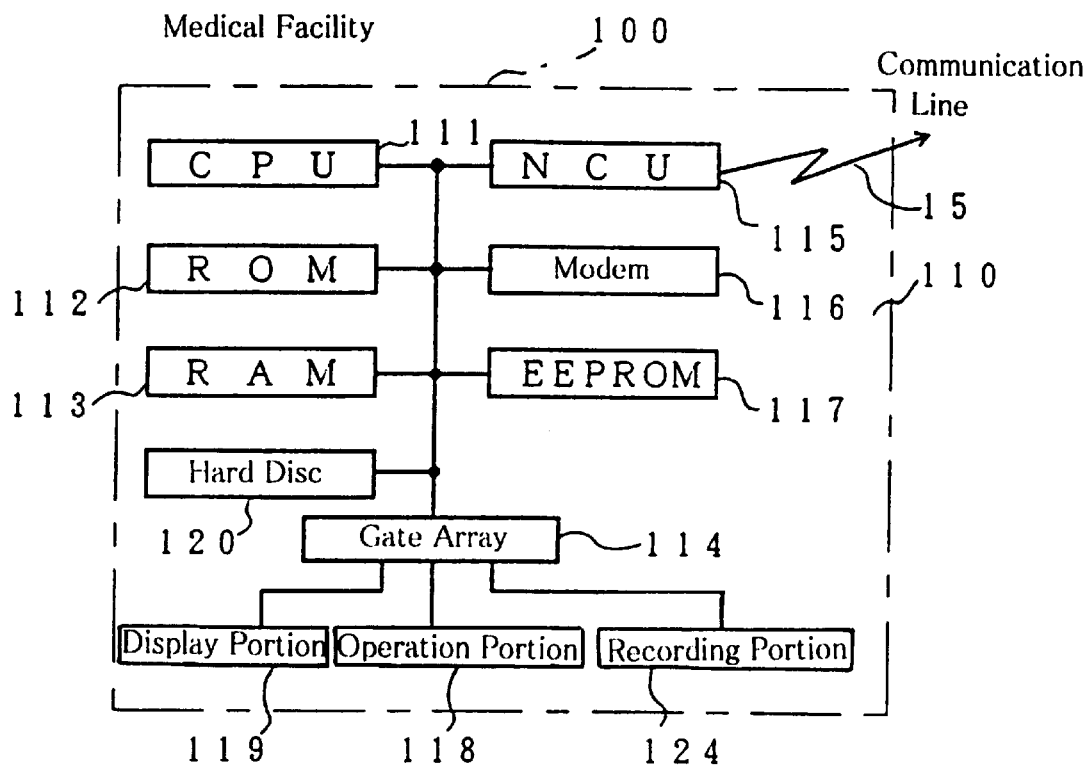
FIG. 8 is a block diagram of a computer to be installed at a medical facility.
Figure 9:
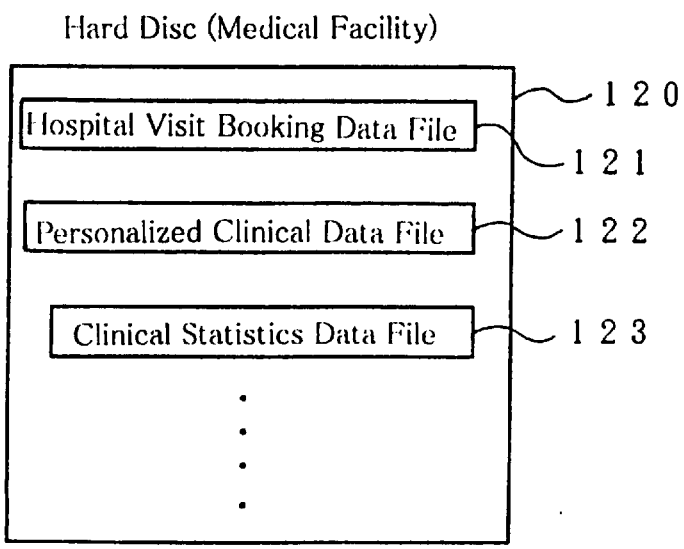
FIG. 9 is a schematic diagram showing a use of a hard disc memory included in the computer to be installed at the medical facility.

FIG. 8 is a block diagram of a computer 110 installed in the medical facility 100 which is accessible by the central controlling unit 20 via the communication line. This computer 110 comprises a CPU 111, a ROM 112, a RAM 113, a sate array 114, an NCU 115, a modem 116, an EEPROM 117, a hard disc 120, an operation portion 118, a display portion 119, and a recording portion 124. As shown in FIG. 9, the hard disc 120 as a large capacity memory includes a booking data file 121, a personalized clinical data file 122, a clinical statistics data file 123, and so on. The booking data file 121 stores data on bookings made for each of clinical departments within the medical facility, being updated with new booking entries made within the medical facility as well as with data-received from the hard disc 240 of the central controlling unit 20 as will be described later.

Next, a flow of actions involving the terminal unit 30, central controlling unit 20, and the computer 110 in the medical facility 100 is described following flowcharts.

Figure 10:
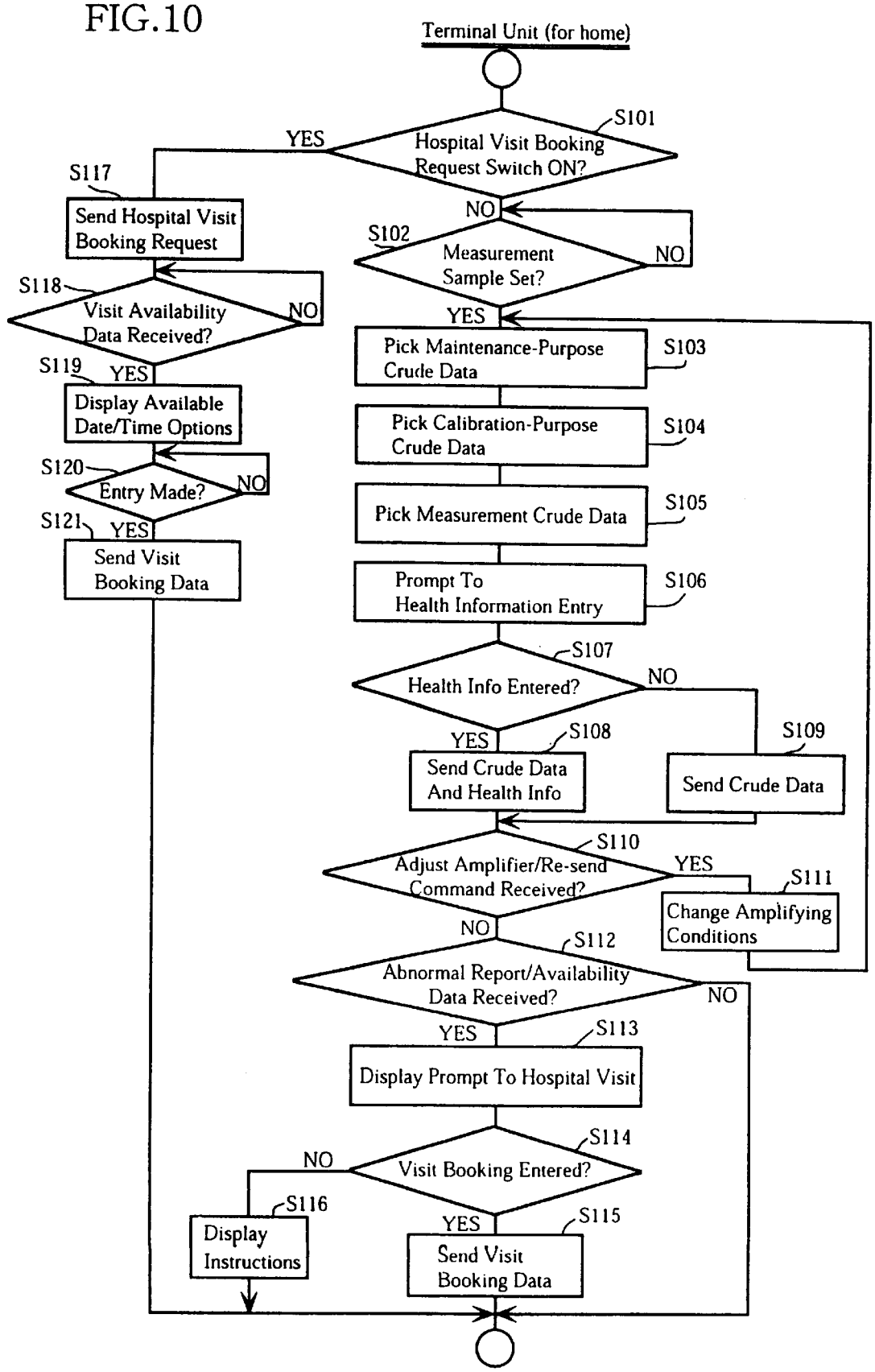
FIG. 10 is a flowchart showing a flow of actions taken by the terminal unit.

FIG. 10 is a flowchart showing a flow of actions performed by the terminal unit 30 installed in the patient's home.

For example, if one of the key switches 386 of the operation/display portion (FIG. 4) of the terminal unit 30 is operated, a judgment is made if the patient is requesting to make a reservation for a hospital visit (S101). If it is judged that the patient is requesting to make the reservation (S101: YES), a hospital booking request signal is sent to the central controlling unit 20 (S117). When booking availability data of the medical facility, which is sent through actions performed by the central controlling unit 20 to be described later, is received (S118: YES), the display portion 39 displays available date and time options (S119). The patient chooses one from the available date and time options displayed on the display portion 39 by depressing a key switch for example. Once the booking entry is thus made (S120: YES), data representing the selected option is sent to the central controlling unit 20 (S121).

If the patient is not requesting to make the reservation (S101: NO), a next step of actions for collecting the clinical testing crude data is performed. Specifically, when the clinical test crude data collecting portion 40 of the terminal unit 30 is loaded with a measurement sample (specimen) (S102: YES), the clinical test crude data collecting portion 40 of the terminal unit 30 automatically makes measurements successively to the standard sample 42A, calibration-purpose sample 42B, and the measurement sample 42, collecting the maintenance-purpose crude data, calibration-purpose crude data and crudemeasurement data respectively (S103, S104, S105) Each of the above crude data is a signal amplified under a predetermined condition by the amplifying portion 48. For example, if the patient is a diabetic, the patient should preferably make it a rule to use a specific time of every morning for collecting and loading his urine to the sample magazine of the terminal unit 30 for the above crude data collecting operation. More specifically, if the crude data collection is to be made by detecting concentration of a specific chemical component present in the urine by means of the spectrum analysis technique as mentioned above, a beam of selected wavelength is passed through the cell containing the loaded urine sample. The clinical test crude data collecting portion 40 then outputs electric signals representing intensity values of the beam of selected wavelength before and after passing the cell.

Next, a display such as shown in FIG. 13(a) is made for prompting the patient to enter his current health status (S1O6). The patient depresses one of the five entry switches 381 through 385, thereby entering his assessment on his current health status in five grades. If the health status is entered (S107: YES), then the above crude data and the entered health status data are sent to the central controlling unit (S108). If there is no entry on the health status (S107: NO), then the above crude data alone is sent to the central controlling unit (S109) after a predetermined amount of time is passed for example.

Next, if command is received from the central controlling unit 20 within a predetermined time for changing amplifying conditions and re-sending the data with respect to the latest transmission of the crude data (S110: YES), then the amplifying conditions are changed according to the command (S111), and steps S103 through S108 are repeated. If the command for changing the amplifying conditions and re-sending the data is not received from the central controlling unit 20 at step S110 (S110: NO), then a next step of actions is performed.

As will be described later, upon receiving the crude measurement data and other information from the terminal unit 30, the central controlling unit 20 calculates the measurement data, which is then forwarded to the personalized clinical data control. If the forwarded data are found abnormal, then the abnormality report describing the found abnormality, and hospital visit booking availability information based on the booking data file at the medical facility are sent as a reply. If such an abnormality report and the booking information are received (S112: YES), then a display such as shown in FIG. 13(b) is made, prompting the patient to make a reservation for a hospital visit (S113). If the patient would like to make the reservation, then he should depress the booking entry key indicated by the numeric code 386 in FIG. 4. When a choice is made for a hospital visit, then available date and time options are displayed as shown in FIG. 13(c) based on the booking availability data, prompting the patient to make a choice. As described above, if the choice is made for making a visit, and then a reservation is entered by selecting a specific day and time from the available options (S114: YES), then a confirming message such as shown in FIG. 13(d) is displayed, and the data including the selected option is sent to the central controlling unit 20 (S115). If no entry is made for reservation (S114: NO), then instruction such as shown in FIG. 13(e) is displayed.

Figure 11:
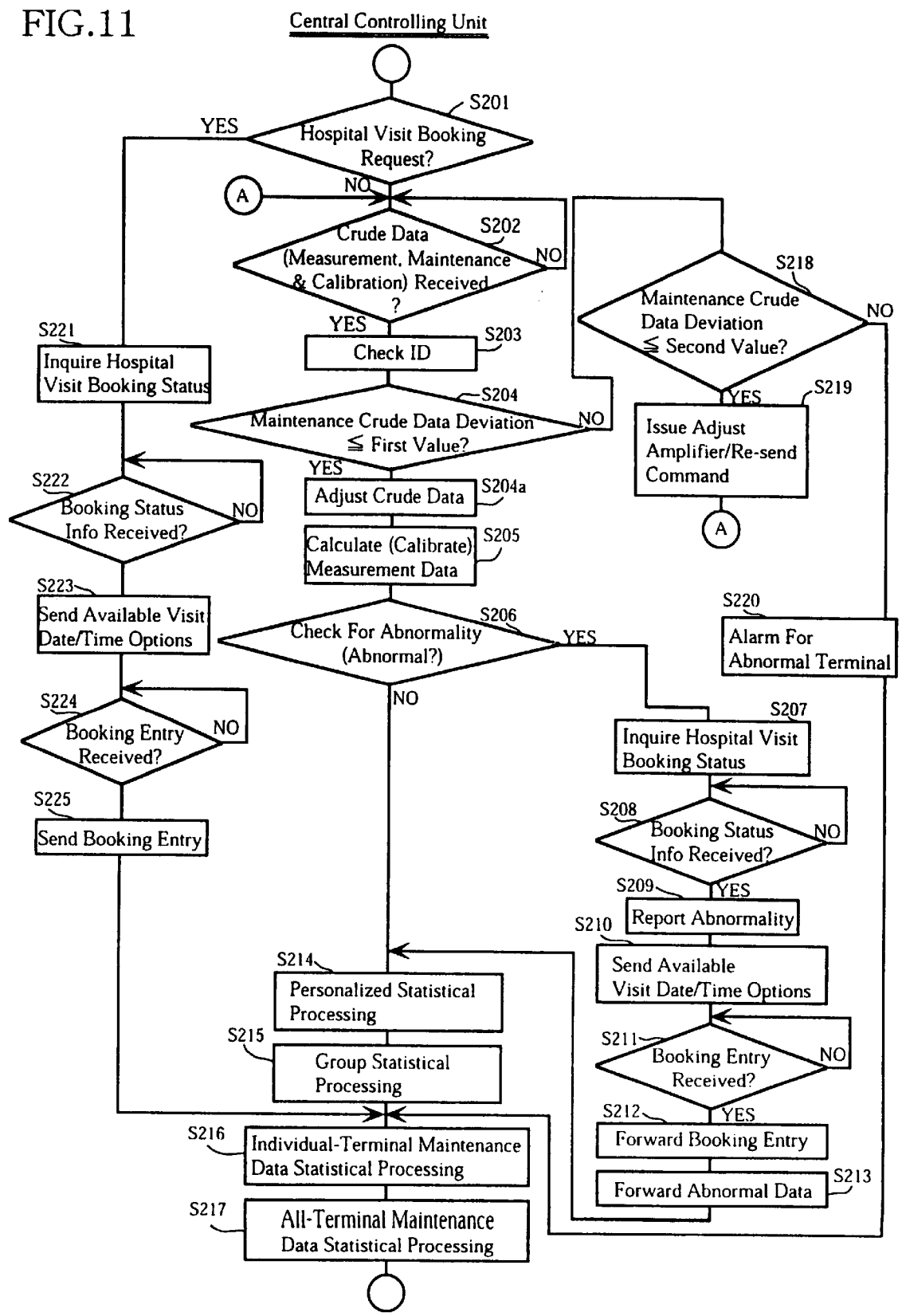
FIG. 11 is a flowchart showing a flow of actions taken by the central controlling unit.
Figure 12:
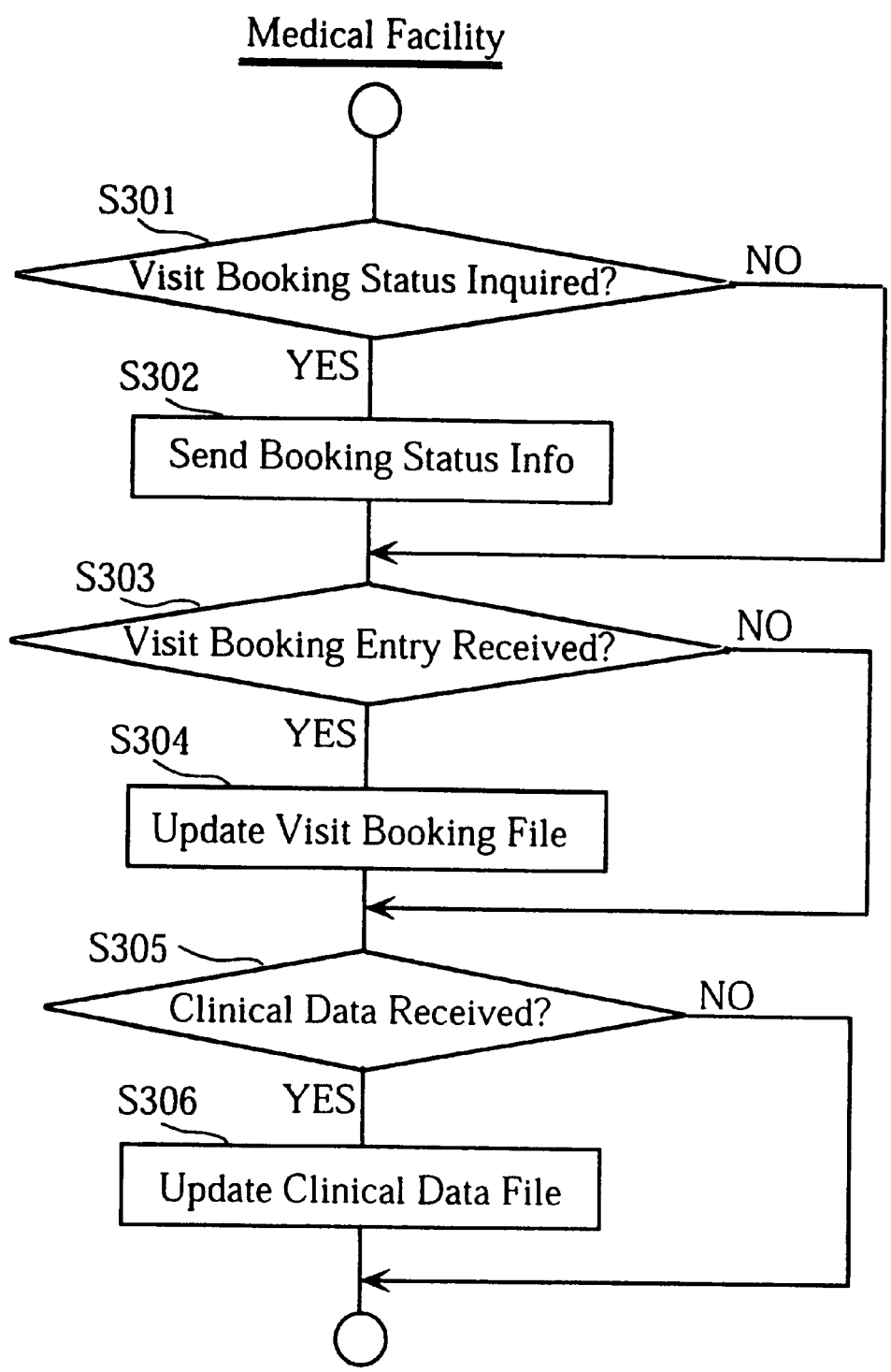
FIG. 12 is a flowchart showing a flow of actions taken by the computer to be installed at a medical facility.

FIG. 11 is a flowchart showing a flow of actions performed by the central controlling unit 20.

If the central controlling unit 20 receives the hospital visit booking request from the terminal unit 30 with respect to the patient's choice for making a hospital booking request made in steps S117 through S121 in FIG. 10 (S201: YES), then the central controlling unit 20 sends the booking status inquiry signal (S221) to the medical facility 100 relevant to the patient. As will be described later, upon such a booking status inquiry, the medical facility 100 makes reference to the facility's booking data file, and responds by sending the booking status information, i.e. data on available date and time for the above request. If such a booking status data is received (S222: YES), then the central controlling unit 20 transfers the data on available date and time options received from the medical facility 100 to the terminal unit 30 (S223). Then, upon receiving the booking entry data from the terminal unit 30 (S224: YES), the booking entry data sent from the terminal unit 30 is forwarded to the medical facility 100 (S225).

On the other hand, if there is not a booking request chosen by the patient (S201: NO), then a next step is performed for calculating the measurement data by using each of the crude data sent from the terminal unit 30. Specifically, if the above crude data, i.e. the maintenance-purpose crude data, calibration-purpose crude data, and crude measurement data are received from the terminal unit 30 (S203: YES), then the data are checked for an accompanying ID code to identify which patient the data represent (S203). Next, the maintenance-purpose crude data is compared with the standard value to see if the deviation equals a first preset value (S204). More specifically, a comparison is made between the standard value predetermined for the crude data which is a value to be obtained from measurement of any of the standardized maintenance-purpose samples loaded to all of the terminal unit 30 and an actual maintenance-purpose crude data sent from the terminal unit 30. If there is any deviation between the two values, it means that the crude data sent from this particular terminal unit 30 contains an error resulting from shift in the output level of the amplifying portion of the terminal unit. If this error is due to a shift in gain at the amplifying portion, then the error can be removed from the measured crude data by first dividing the value of maintenance purpose crude data by the standard value to obtain a coefficient of the error, and then dividing the value of crude measurement data by this coefficient. If the deviation between the standard value and the maintenance-purpose crude data is found not greater than the first preset value in step S204 (S204: YES), then step S204 is performed for adjusting the measurement crude data, and the error is eliminated from the crude measurement data by using the above coefficient of error. It should be noted here that differences in the output level among the plurality of amplifying portions 48 may not only result from the shift in the gain as mentioned above but also result from difference in the amount of offset. In order to adjust the output level in the latter case, at least two standard samples have to be measured for clarifying linear characteristics of the amplifying portion, so that the crude measurement data can be adjusted according to the found linear characteristics. It should be noted further that the adjustment has to be made not only to the crude measurement data obtained from the measurement sample but also to the calibration-purpose crude data obtained from the calibration sample because both are the output from the amplifying portion where there is the shift in the output level.

Next, the crude measurement data adjusted as above is used for calculating (calibrating) the measurement data (S205). Specifically, adjusted calibration-purpose crude data from two calibration samples are used for making a calibration curve, from which concentration of the specific chemical component in the urine corresponding to the value of crude measurement data is calculated.

The measurement data thus obtained as the clinical data is then checked to see if the data is normal with respect to the normal range for this particular patient or the normal range for the group which this particular patient belongs to. If there is accompanying information, i.e. the patient's personal assessment on his current health status, such information is also referred to in judging if the clinical data obtained as above is normal with respect to the normal range for this particular patient or the normal range for the group which this particular patient belongs to (S206). When the data is found abnormal (S206: YES), then necessary actions such as the issuance of the abnormality report and prompting the patient to a visit (S207 through S213) are performed. According to the present embodiment, if the obtained clinical data is found abnormal, then the patient should visit the medical facility to see his attending physician for examination. Therefore, upon finding the abnormality of the data, the booking status inquiry signal is automatically sent to the relevant medical facility 100 (S207). Then, upon receiving available date and time options for the visit (S208: YES), data on the available date and time options for the visit is sent (S210). Then, upon receiving the abnormality report as well as the available date and time options for the visit, the terminal unit 30 takes actions for prompting the patient to make the visit as already described above.

If the booking entry data is received from the terminal unit 30 (S211: YES), then the booking entry data, which represents the date and time of visit selected by the patient, is forwarded to the medical facility 100 (S212). It should be noted that the abnormality report made at step S209 should also be forwarded to the medical facility. Thus, if abnormality is found, the clinical data found to be abnormal are forwarded to the medical facility for examination by the attending physician (S213).

Regardless of whether abnormality is found or not, all of the clinical data calculated by using the clinical test crude data sent from the terminal unit 30 are passed to the personalized statistical processing (S214) and the group statistical processing (S215). Specifically, in the personalized statistical processing, the clinical data is accumulated by the ID cord for performing statistical processing. By accumulating the clinical data on a personal basis, it becomes possible to determine a range of normality for each of the at-home patients. Such a range of normality is generally narrower than that for a group. Thus, by checking the clinical data against this personalized norm every time the clinical data collection is made, it becomes possible to closely monitor the health status of each at-home patient. Further, the group statistical processing performs predetermined statistical processing for the group of patients regardless of the ID, providing the range of normality for the group.

If the maintenance-purpose crude data is found in step S204 as having a deviation from the standard greater than the first preset value (S204: NO), then the deviation is further checked if not greater than a second preset value (S218). The second preset value is generally set to be greater than the first preset value. If the above deviation is not greater than the second value (S218: YES), then the command for changing the amplifying conditions and re-sending the data is sent to the terminal unit 30 (S219). Specifically, according to the present embodiment, if the shift in the output level of the maintenance-purpose crude data sent from the terminal unit 30 is relatively small, then the correction is made by adjusting the crude data within the central controlling unit 20 as already described. On the otherhand, if the shift is relatively large, then the correction is made by changing the amplifying conditions of the amplifying portion 48 of the terminal unit 30 instead of adjusting the crude data within the central controlling unit 20. Upon receiving the command for changing the amplifying conditions and re-sending the data, the terminal unit takes the actions already described above. When the crude measurement data and the calibration-purpose crude data after having changed the amplifying conditions are received from the terminal, then the steps S202 through S204 are performed again.

If the maintenance-purpose crude data is found in step S218 to be greater than the second preset value (S218: NO), then the terminal unit 30 is judged to be in need of maintenance service, and a terminal abnormality alarm is issued (S220). Specifically, This terminal abnormality alarm is issued to a company maintaining this dispersed-type health care system, the terminal unit, and related medical facilities and so on so that necessary actions are taken for preventing a medical malpractice.

History of the maintenance-purpose crude data and changes in the amplifying conditions is passed to the individual-terminal maintenance-data statistical processing (S216), where records are maintained for historical change of the deviation from the norm and how the amplifying conditions are changed, for example. Through such a statistical processing, it becomes possible for example to make forecast a trend of change in the maintenance-purpose crude data deviation, which makes possible to forecast timing for the maintenance service to be made to the terminal unit 30 for example.

The history of maintenance-purpose crude data and change in the amplifying conditions is also passed to the all-terminal maintenance-data statistical processing (S217). This makes possible to clarify an overall trend of the deviation of the maintenance-purpose crude data from the norm. Such information can be effectively used in maintaining the system.

FIG. 13 is a flowchart showing operations to be taken by the computer installed in the medical facility.

Upon receiving the booking request (S301: YES), booking status information, i.e. data on available date and time options for the above request obtained through reference to the medical facility's booking data file, is sent to the central controlling unit 20 (S302). Then, upon receiving via the central controlling unit 20 the booking entry data selected by the patient at the terminal unit 30 (S303: YES), the booking data file 121 is updated (S304), completing the booking for the patient's visit to the medical facility 100. Further, upon receiving the clinical data for examining the health status of the patient from the central controlling unit 20 (S305: YES), the personalized clinical data file (Numeric code 122, FIG. 9) is updated as predetermined.

Figure 14:
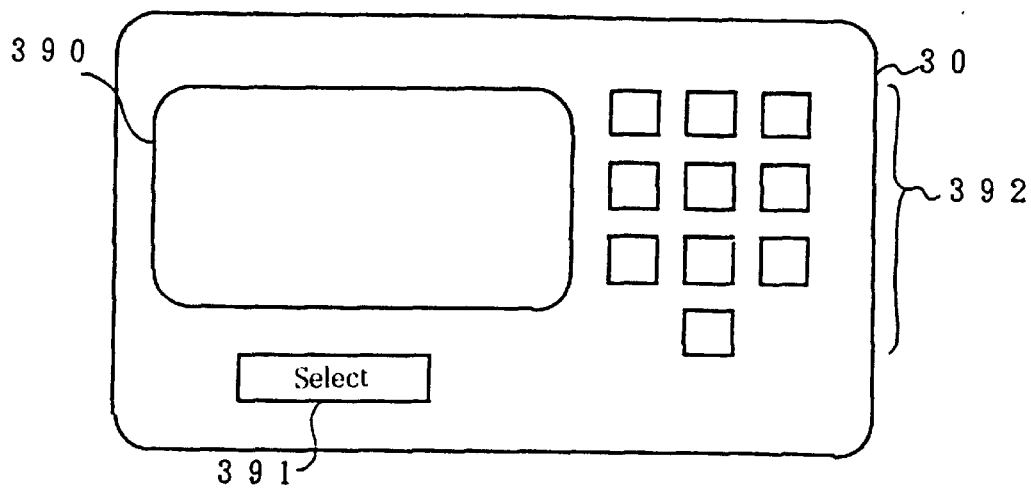
FIG. 14 shows some sample displays to be made on the operation/display portion of the terminal unit to be installed at a clinic.

Now, in general it is assumed that the terminal unit 30 is installed at a home of an at-home patient. However, the installation may be made at a small-scale clinic of a depopulated area for example. FIG. 14 shows an operation/display portion of the terminal unit 30 to be installed at such a clinic. This operation/display portion includes an LED panel 390 for displaying various information, a selection key 391, and a set of key switches 392 for entering data. This allows a physician at the clinic to set a specimen so that clinical testing measurement crude data can be sent by the terminal unit 30 to the central controlling unit 20, and further, to send additional information. Specifically, for a patient suffering from a liver disease for example, numerical data collected by the physician such as GPT and GOT can be entered through the ten-keys 392 as the additional information to be sent to the central controlling unit 20. In such a case the central controlling unit 20 can have a more accurate grasp of the patient's health status by referring to the above additional information. Such additional information can be entered very simply by first depressing the selecting key 391 until a category of information to be sent is displayed, and then by typing the numeric value on the key switches 392.

Figure 15:
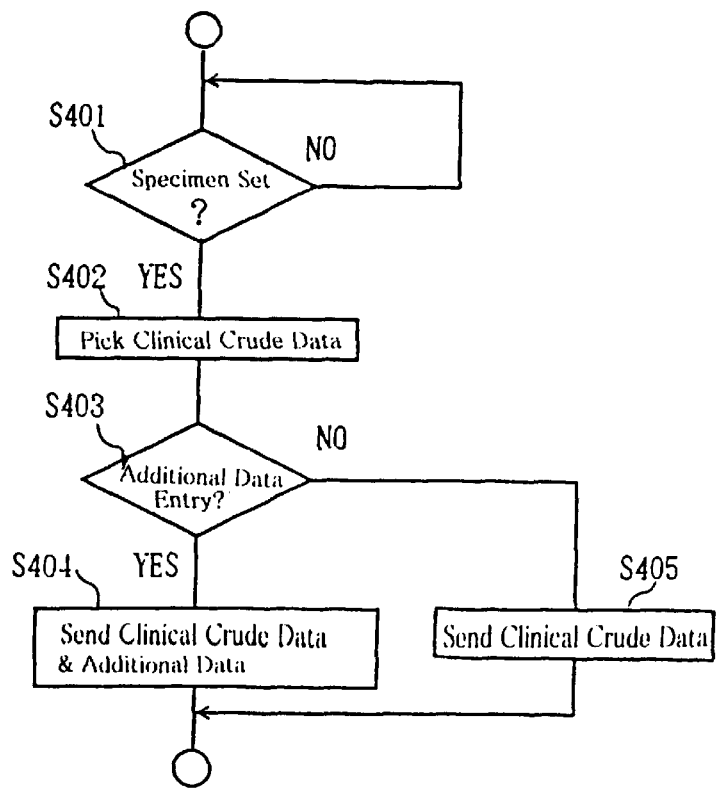
FIG. 15 is a flowchart showing a flow of actions taken by the terminal unit to be installed at the clinic.

FIG. 15 is a flowchart showing a flow of process made by the terminal suitably made for installation in such a clinic as described above.

When the specimen is loaded (S401: YES), the terminal unit 30 automatically collects the clinical testing crude data (S402). Then, if additional information is entered (S403: YES), the clinical testing crude data and the additional information are sent to the central controlling unit 20. If no additional information is entered (S403: NO), then only the clinical testing crude data is sent to the central controlling unit 20.

As described above, according to the dispersed-type health care system 10 of the present embodiment, the clinical test crude data collecting portion 40 provided in the terminal unit 30 and clinical data calculating means 210 provided in the central controlling unit 20 work together providing the function of a clinical testing apparatus. Specifically, the central processing unit takes the part of performing complex analytical operation on the crude data for obtaining the clinically meaningful data. Hence, the terminal unit 30 to be installed at a patient's home can have a simple and inexpensive configuration comprising only minimum necessary functions for collecting crude data, transmitting the data, and performing simple input/output operation. Thus, according to such a terminal unit as the terminal unit 30, it becomes possible to reduce economic burden on patients hoping to have an at-home medical monitoring service or at-home medical support service of the above kind.

Further, a capability of providing an inexpensive terminal such as the above has a significant meaning in terms of clinical data statistics. Specifically, a more accurate clinical data statistics can become possible on a group of data sent from a large number of terminals installed at patient's home, clinics and other locations.

Further, the dispersed-type health care system 10 according to the above embodiment includes; the personalized statistical processing means 223 for statistically processing personal clinical data for determining a normal range for each individual assigned with the terminal unit 30; the abnormality judging means 226 for judging if the clinical data calculated from the crude data sent from each terminal unit 30 is abnormal or not with respect to the normal range for the group and/or the normal range for the relevant individual; the abnormality reporting means 224 for issuing an abnormality report to the terminal unit 30 and/or the medical facility if data are found abnormal; and the abnormal-data forwarding means 225 for forwarding the abnormal data to the medical facility; and the hard disc 240 which allows the patient to use the terminal for voluntarily making a reservation to his relevant medical facility for his visit, prompts the patient to make a reservation for his visit when his clinical data are found abnormal, and automatically perform the reservation procedure according to a data entry performed following the above prompt. As a result, it becomes possible to provide even more refined health care to the at-home patients.

Further, according to the present embodiment, the terminal unit 30 includes the health information entry portion 46 through which patient's current health status can be entered. This makes possible to grasp more clearly current health condition of the at-home patients.

Still further, according to the present embodiment, errors in data resulting from different output levels among the terminal units 30 can be virtually eliminated by a simple method, for example, of having each of the terminal unit 30 measure the standard sample 42A of the same standard for obtaining maintenance-purpose crude data, having the central controlling unit compare each maintenance-purpose crude data with the standard value, and adjusting each crude measurement data according to the result of comparison. As a result, it becomes possible to remarkably improve reliability of the measured data as clinical data to be accumulated within the central controlling unit for grasping health status of each patient as well as for statistical purposes. Further, maintenance of each terminal becomes remarkably simplified when operating the dispersed-type testing/measuring system with a huge number of the terminal unit 30 connected to the central controlling unit via communication lines. Such a dispersed-type testing/measuring system based on central control, with a huge number of terminals and with high reliability becomes available for the first time by the present invention.

Figure 16:
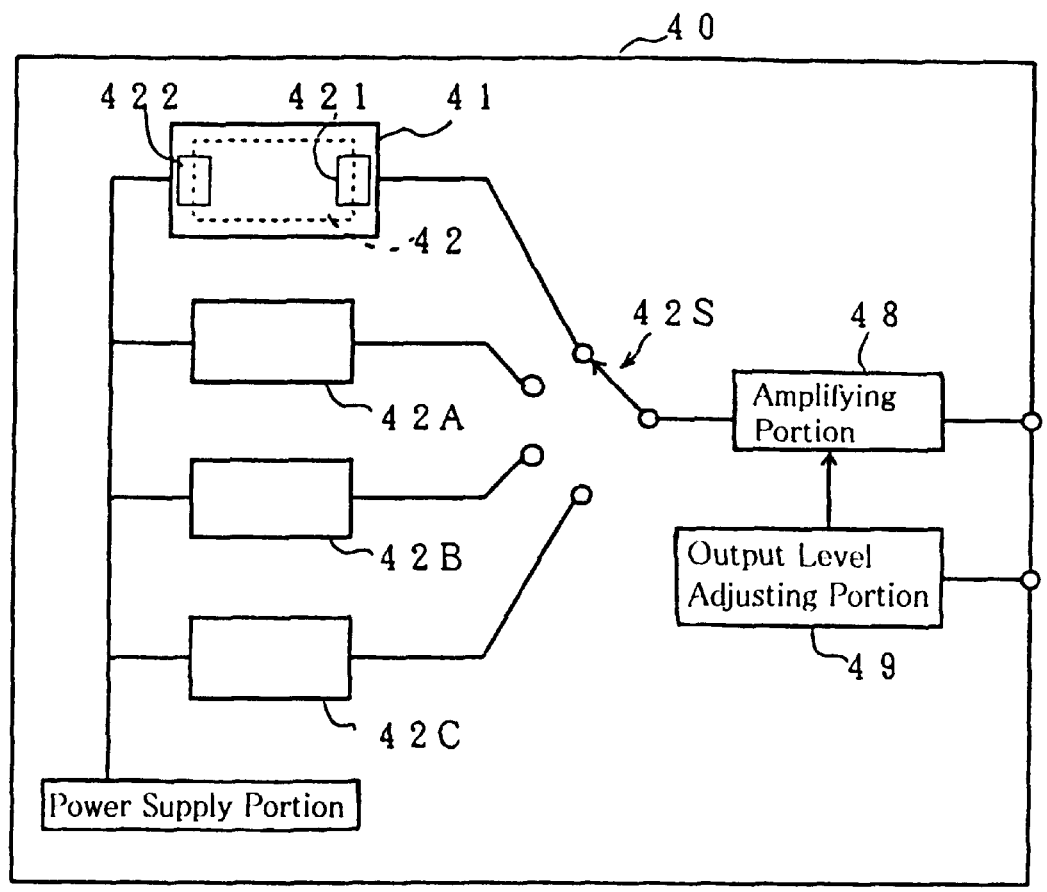
FIG. 16 is a schematic diagram showing another configuration of the crude data collecting portion included in the above terminal unit.

Scope of the present invention is of course not limited by the embodiment described above. For example, the crude data collecting portion included in the terminal unit 30 according to the present embodiment makes measurements for a specific chemical component contained in the sample by a spectrum analytic method as shown in FIG. 3. However, the crude data may alternatively collected by means of an electrochemical method as shown in FIG. 16. Specifically, a sample magazine 41, including a measuring electrode 421 and a pairing electrode 422, is disposed parallel with a plurality of standard resistors 42A, 42B, 42C. The sample magazine 41 and the standard resistors 42A, 42B, 42C are selectively switched by a selecting switch 425 to an amplifying portion 48. Output level of the amplifying portion 48 can be adjusted by an output level adjusting portion 49 according to the command from the central controlling unit. In the above example, one or more of the plurality of resistors will function as the standard sample, whereas one or more of the plurality of resistors function as the sample for calibrating data.

Further, the present invention of course includes in its scope of the invention a case in which a plurality of chemical components contained in urine are quantified simultaneously by a multivariate regression analysis as a means for calibration at the central controlling unit by using calibration-purpose data.

Further, according to the above embodiment, crude data of the standard sample, i.e. crude data for the maintenance of the terminal unit, are collected and sent every time the crude data is collected from the measurement sample at the terminal. Alternatively, for example, the maintenance-purpose crude data may be collected and sent consecutively according to a command from the central controlling unit, or the maintenance-purpose crude data may be collected and sent to the central controlling unit periodically.

Further, according to the above embodiment, clinical data are obtained from analytical measurement on a specific chemical component contained in urine. The subject of testing is of course not limited to this, but may include blood, exhalation, sweat, or other body fluids from which a specific component may be analyzed for obtaining clinical data.

What is claimed is:

1. A dispersed-type testing/measuring system comprising:
a central controlling unit and a plurality of terminal units each accessible to the central controlling unit via a communication line;
wherein each of the terminal units includes a data collecting portion for collecting measurement data, maintenance-purpose data and calibration-purpose data respectively from a measurement sample, a standard sample and a calibration sample; an amplifying portion for amplifying and outputting the collected data; an output level adjusting portion for adjusting output level of the amplifying portion; and a data sending means for sending the data amplified by the amplifying portion to the central controlling unit;
wherein the central controlling unit includes a data calculating means for processing the measurement data, maintenance-purpose data and calibration-purpose data received from each of the terminal units; and an output level adjusting means for sending an output level adjusting command to the output level adjusting portion of each terminal unit and further the central controlling unit includes statistical processing means for determining a range of normality for a group of patients by processing the clinical data from the plurality of terminal units;

wherein the data calculating means determines a deviation of the maintenance-purpose data from standard data, and calibrates the measurement data by using the calibration-purpose data if the deviation is determined to be not greater than a first preset value;

and the data calculating means, alternatively, sends the output level adjusting command for adjusting the output level of the output level adjusting portion of a terminal unit via the output level adjusting means if the deviation is determined to be greater than the first preset value but not greater than a second preset value.

2. The dispersed-type testing/measuring system according to claim 1, wherein the central controlling unit further includes an alarming means or alarming each terminal unit if the deviation is greater than the second preset value.

3. The dispersed-type health care system according to claim 1, wherein each of the terminal units assigned to a patient or a facility related to the patient, wherein the data collecting portion of each terminal unit is designed to collect clinical data related to the patient, and wherein the central controlling unit further includes personalized clinical data maintaining means for monitoring health status of the patient.

4. The dispersed-type health care system according to claim 3, wherein each terminal unit further includes an information entering portion for entering health status data of the patient and for sending the health status data to the central controlling unit through the data sending means.

5. The dispersed-type health care system according to claim 4, wherein the personalized clinical data maintaining means includes personalized statistical processing means for determining a personalized range of normality for the patient by statistically processing the personalized clinical data.

6. The dispersed-type health care system according to claim 5, wherein the personalized clinical data maintaining means further includes an abnormality judging means for determining abnormality if the clinical data sent by each terminal unit deviate from the personalized range of normality established for the patient.

7. The dispersed-type health care system according to claim 6, wherein the abnormality judging means makes abnormality determination by taking into account the health status data entered at the information entering portion of each terminal unit.

8. The dispersed-type health care system according to claim 6, wherein the personalized clinical data maintaining means further includes an alarming means for sending an abnormality report to a relevant terminal unit if the abnormality judging means makes the abnormality determination.

9. The dispersed-type health care system according to claim 6, wherein the personalized clinical data maintaining means further includes an abnormal-data forwarding means for forwarding the clinical data of the patient to a medical facility accessible by the central controlling unit via the communication line if the abnormality judging means makes the abnormality determination.

10. The dispersed-type health care system according to claim 1, wherein the personalized clinical data maintaining means includes an abnormality judging means for determining abnormality if the clinical data sent by each at the end of the plurality of termimal units deviate from the range of normality for the group.

* * * * *